United States Patent [19]

Delevalleé et al.

[11] Patent Number: 4,522,816

[45] Date of Patent: Jun. 11, 1985

[54] ANALGESIC TREATMENT AND COMPOSITIONS

[75] Inventors: Francoise Delevalleé, Vincennes; Roger Deraedt, Pavillons-sous-Bois, both of France

[73] Assignee: Roussel Uclaf, Paris, France

[21] Appl. No.: 543,270

[22] Filed: Oct. 19, 1983

[30] Foreign Application Priority Data

Oct. 26, 1982 [FR] France ................. 82 17892

[51] Int. Cl.³ ............. A61K 27/00; A61K 31/46; A61K 31/68; A61K 31/445; A61K 31/485
[52] U.S. Cl. ...................................... 514/52
[58] Field of Search ........................... 424/201

[56] References Cited

U.S. PATENT DOCUMENTS 3,072,809  3/1965  Montandraud ................. 424/232

Primary Examiner—Stanley J. Friedman
Attorney, Agent, or Firm—Charles A. Muserlian

[57] ABSTRACT

Novel analgesic compositions comprising a central analgesic and an amount of vitamin $B_{12}$ or a derivative thereof sufficient to potentialize the central analgesic with reduced toxicity and an improved method for treating pain in warm-blooded animals, including humans.

14 Claims, No Drawings

ANALGESIC TREATMENT AND COMPOSITIONS

STATE OF THE ART

Central analgesic or narcotics are classically considered to have the same characteristics as morphine which provokes toxicomania and lead to respiratory depression. The synthesized derivatives of morphine that have been therapeutically used include pethidine, dextromoramide and pentazocine and these compounds have the same disadvantages as morphine. Research for compounds having a strong analgeic effect but devoid of toxicomonogenic activity has not been successful.

OBJECTS OF THE INVENTION

It is an object of the invention to provide novel analgesic compositions having potentialized activity and reduced toxicity.

It is another object of the invention to provide an improved process for treating pain in warm-blooded animals.

These and other objects and advantages of the invention will become obvious from the following detailed description.

THE INVENTION

The improved analgesic compositions of the invention are comprised of a central analgesic and an amount of vitamin $B_{12}$ or a derivative thereof sufficient to potentialize the central analgesic.

Examples of suitable derivatives of vitamin $B_{12}$ or cyanocobalamine useful in the compositions of the invention are hydroxocobalamine, nitrocobalamine, methylcobalamine, coenzyme of vitamin $B_{12}$ or dibencozide and physiological forms of directly active vitamin $B_{12}$ without transformation.

Vitamin $B_{12}$ and its derivatives are known to play a very important role in humans in the course of diverse biochemical processes requiring the presence of this vitamin. They are useful, for example, for the treatment of asthenia, anemias and emaciation. The said compounds are also known to possess antalgic properties when administered to humans in large doses.

The association of vitamin $B_{12}$ and its derivatives with a central analgesic was not known before now and the compositions of the invention have a susperior analgesic activity than the analgesic alone. Animal tests have shown the potentialization effect of an analgesic of the invention when a non-analgesic dose of an equivalent of vitamin $B_{12}$ is administered.

In the compositions of the invention the analgesic can be present at an analgesic or non-analgesic dose. The compositions give an important analgesic activity using an amount of the central analgesic less than the amount necessary to obtain the same activity and diminishes as well the side effects of the central analgesic used.

The central analgesic used in the compositions is preferably morphine or a synthetic derivative succedaneous of morphine, especially pethidine, dextromoramide or pentazocine. The known undesired effects of the administration of this morphine type of analgesic at the usually used doses are (a) nausea and vomitting, (b) constipation, (c) respiratory depression, (d) physical and/or psychic dependence in the course of prolonged treatment, (e) symptoms of failure to stop treatment including mydriasis, muscular contractions, cephalea, perspiration, vomitting, diarrhea, tachycardia, polypnea, hyperthermia, hypertension, etc.

The synergistic analgesic activity obtained by the compositions of the invention is shown particularly when used for reducing physical and psychic dependence as well as by the accustoming development following repeated administrations of analgesics of the morphine type. One speaks of the association of vitamin $B_{12}$ or a derivative thereof with a morphinic analgesic as an "economizer of morphine".

In preferred compositions of the invention, the central analgesic is morphine and the second ingredient is selected from the group consisting of vitamin $B_{12}$, hydroxocobalamine, nitrocobalamine, methylcobalamine and coenzymes of vitamin $B_{12}$, especially dibencozide. The associations permit a reduction of about 2 to 4 times the dose of morphine used to obtain the same effect. The potentialization effect is also observed with analgesics other than morphine such as a substituted derivative of enkephaline, 5-hydroxytryptophane and precursor of serotonine which is a mediator of pain reactions.

The compositions of the invention are useful for the treatment of intense pains, in particular rebelling against peripheric antalgesics such as in the course of neoplasic processes, in the treatment of pancreatics, nephretic or biliary colics, in the treatment of post operative and post traumatic operations.

The compositions may be in the form of tablets, dragees, gelules, capsules, granules, suppositories and injectable solutions or suspensions. Examples of suitable excipients are talc, arabic gum, lactose, starch, magnesium stearate, aqueous and non-aqueous vehicles, fats of animal or vegetable origin, paraffinic derivatives, glycols, diverse wetting agents, dispersants or emulsifiers and preservatives.

The preferred ratio of central analgesic to vitamin $B_{12}$ or derivative is 1 to 1 to 5 parts by weight and the compositions can be used to reduce by 2 to 4 times the amount of analgesic used. For example, if the usual parenteral daily dose of central analgesic alone in the adult is 0.005 to 0.03 g, the dose of morphine associated with dibencozide is 0.001 to 0.01 g.

The novel method of the invention for treating pain in warm-blooded animals, especially humans, comprises administering to warm-blooded animals, an analgesically effective amount of a central analgesic and an amount of vitamin $B_{12}$ or a derivative thereof sufficient to potentialize the central analgesic.

The two constituents of the compositions of the invention can be administered as a mixture, prepared immediately or not. They can also be administered successively with a time-interval from several seconds up to one or two hours or more (up to 15 hours).

The compositions may be administered orally, rectally or parenterally and the dose will vary depending on the specific analgesic and vitamin $B_{12}$ compound used.

In the following examples there are described several preferred embodiments to illustrate the invention. However, it should be understood that the invention is not intended to be limited to the specific embodiments. cl EXAMPLE 1

An injectable solution was prepared extemporaneously containing 20 mg of lyophilized dibencozide and 2 ml of an injectable solution of 0.25% by weight of morphine hydrochloride. The injectable solution was prepared at the time of use by introducing the injectable solution of morphine hydrochloride into the lyphilized dibencozide and stirring the mixture.

A second injectable solution was prepared containing 5 mg of morphine hydrochloride, 5 mg of cyanocobalamine and 2 ml of sterile solvent.

PHARMACOLOGICAL DATA

A. Potentialization of Analgesic Activity

Male rats weighing about 110 g were placed one by one on a copper plate maintained at 56° C. and the reaction of pain was manifested by the licking of a paw or by jumping of the animal. The time of this reaction was noted and the rats reacting in less than 10 seconds were not used. The rats were divided into homogenous groups with one group not receiving the vehicle of the test compounds. The dibencozide was administered subcutaneously at an inactive dose of 10 mg/kg. 30 minutes before the varying doses of morphine hydrochloride administered subcutaneously also. Under the same treatment conditions, one group did not receive dibencozide and another group did not receive morphine hydrochloride. The reaction of the rats to pain was taken 30, 60 and 90 minutes after treatment. Under these conditions, dibencozide diminished the dose of morphine necessary to double the time of reaction of the rats to pain to 2.7 mg/kg as compared to 7.3 mg/kg for morphine alone.

B. Activity with 5-Hydroxy-Tryptophane (5-HTP)

Using rats weighing about 110 g and the test procedure of Step A, after subcutaneous administration of a dose of 200 mg/kg of 5-HTP considered to be inactive, 10 mg/kg of dibencozide were administered subcutaneously and the hot plate test was administered and readings were taken 90, 120 and 150 minutes. The results of Table I show that the combination had an analgesic activity.

TABLE I

| Compound administered | readings after minutes | | |
|---|---|---|---|
| | 90 | 120 | 150 |
| 5-HTP | 24 | 16 | 34 |
| dibencozide | 0 | 7 | 23 |
| 5-HTP + dibencozide | 82 | 71 | 84 |

C. Potentialization of Analgesic Activity of an Enkephaline

Using mice and the hot plate test of A, dibencozide was administered subcutaneously at a dose of 10 mg/kg 45 minutes before the intracerebroventricular injection of 0.25 mg/kg of D Ala$^2$-Met$^5$-enkephaline or E and the increase in analgesic effect after 15 minutes in % of reaction time was determined.

TABLE II

| Compound administered | % increase in reaction time |
|---|---|
| E | 29 |
| dibencozide + E | 114 |

Various modifications of the compositions and method of the invention may be made without departing from the spirit or scope thereof and it is to be understood that the invention is intended to be limited only as defined in the appended claims.

What we claim is:

1. An analgesic composition comprising a central analgesic selected from the group consisting of morphine, pethidine, dextromoramide and pentazocine and an amount of a vitamin $B_{12}$ component selected from the group consisting of vitamin $B_{12}$, hydroxocobalamine, nitrocobalamine, methylcobalamine, dibenzozide and coenzyme of vitamin $B_{12}$ sufficient to potentialize the central analgesic.

2. A composition of claim 1 wherein the central analgesic is morphine.

3. A composition of claim 1 wherein the central analgesic is selected from the group consisting of pethidine, dextromoramide and pentazocine.

4. A composition of claim 1 wherein the vitamin $B_{12}$ component is selected from the group consisting of vitamin $B_{12}$, hydroxocobalamine, nitrocobalamine, methylcobalamine and coenzyme of vitamin $B_{12}$.

5. A composition of claim 1 wherein the vitamin $B_{12}$ component is dibencozide.

6. A composition of claim 2 wherein the vitamin $B_{12}$ component is dibencozide.

7. A composition of claim 1 wherein the ratio of analgesic to vitamin $B_{12}$ component is 1 to 1 to 5 parts by weight.

8. A method of relieving pain in humans comprising administering to humans an analgesically effective amount of a composition of claim 1.

9. A method of claim 8 wherein the central analgesic is morphine.

10. A method of claim 8 wherein the central analgesic is selected from the group consisting of pethidine, dextromoramide and pentazocine.

11. A method of claim 8 wherein the vitamin $B_{12}$ component is selected from the group consisting of vitamin $B_{12}$, hydroxocobalamine, nitrocobalamine, methylcobalamine and coenzyme of vitamin $B_{12}$.

12. A method of claim 8 wherein the vitamin $B_{12}$ component is dibencozide.

13. A method of claim 9 wherein the vitamin $B_{12}$ component is dibencozide.

14. A method of claim 8 wherein the ratio of analgesic to vitamin $B_{12}$ component is 1 to 1 to 5 parts by weight.

* * * * *